United States Patent
Doerr et al.

(10) Patent No.: US 11,819,696 B2
(45) Date of Patent: Nov. 21, 2023

(54) IMPLANTABLE MEDICAL DEVICE FOR STIMULATING THE HIS BUNDLE OF A HUMAN OR ANIMAL HEART EMPLOYING AN IMPROVED DISTINCTION BETWEEN ATRIAL AND VENTRICULAR SIGNALS DETECTED AT THE HIS BUNDLE

(71) Applicant: BIOTRONIK SE & Co. KG, Berlin (DE)

(72) Inventors: Thomas Doerr, Berlin (DE); Sergey Ershov, Berlin (DE); Torsten Radtke, Berlin (DE); Ulrich Busch, Berlin (DE); Peter Schneider, Berlin (DE); Stefan Paule, Drosendorf (DE); Frank Becker, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 17/770,201

(22) PCT Filed: Oct. 22, 2020

(86) PCT No.: PCT/EP2020/079741
§ 371 (c)(1),
(2) Date: Apr. 19, 2022

(87) PCT Pub. No.: WO2021/078851
PCT Pub. Date: Apr. 29, 2021

(65) Prior Publication Data
US 2022/0387798 A1 Dec. 8, 2022

(30) Foreign Application Priority Data
Oct. 24, 2019 (EP) .................................... 19205046

(51) Int. Cl.
*A61N 1/36* (2006.01)
*A61N 1/365* (2006.01)
(Continued)

(52) U.S. Cl.
CPC ........ *A61N 1/36521* (2013.01); *A61B 5/0538* (2013.01); *A61N 1/056* (2013.01);
(Continued)

(58) Field of Classification Search
CPC .... A61N 1/36521; A61N 1/056; A61N 1/365; A61N 1/36585; A61N 1/368;
(Continued)

(56) References Cited

U.S. PATENT DOCUMENTS

2012/0239106 A1\* 9/2012 Maskara ................ A61N 1/371
607/28
2019/0126050 A1 5/2019 Shuros et al.
(Continued)

FOREIGN PATENT DOCUMENTS

EP 3431135 A1 1/2019

OTHER PUBLICATIONS

International Search Report (PCT/ISA/210) and Written Opinion (PCT/ISA/237) dated Jan. 28, 2021, by the European Patent Office as the International Searching Authority for International Application No. PCT/EP2020/079741.

*Primary Examiner* — Rex R Holmes
(74) *Attorney, Agent, or Firm* — Buchanan Ingersoll & Rooney PC

(57) ABSTRACT

An implantable medical device for stimulating a human or animal heart. In operation, the device performs the following steps: a) sensing an atrial electric signal a the first detection unit; b) sensing an electric signal at the His bundle with a second detection unit upon termination of a first time period starting upon sensing the atrial electric signal with the first
(Continued)

detection unit and/or starting upon applying a stimulation pulse, wherein the first time period lies in a range of from 10 ms to 100 ms; c) classifying the electric signal sensed with the second detection unit as His bundle activity signal or as ventricular activity signal.

9 Claims, 3 Drawing Sheets

(51) Int. Cl.
    *A61N 1/05*     (2006.01)
    *A61N 1/372*     (2006.01)
    *A61N 1/368*     (2006.01)
    *A61N 1/375*     (2006.01)
    *A61B 5/0538*     (2021.01)

(52) U.S. Cl.
    CPC .............. *A61N 1/365* (2013.01); *A61N 1/368* (2013.01); *A61N 1/3684* (2013.01); *A61N 1/36585* (2013.01); *A61N 1/3752* (2013.01); *A61N 1/37223* (2013.01); *A61N 1/37235* (2013.01); *A61N 1/37247* (2013.01); *A61N 1/37252* (2013.01)

(58) Field of Classification Search
    CPC .............. A61N 1/3684; A61N 1/37223; A61N 1/37235; A61N 1/37247; A61N 1/37252; A61N 1/3752; A61N 1/37264; A61N 1/372; A61B 5/0538; A61B 5/29; A61B 5/4836; A61B 5/363; H01R 13/465
    See application file for complete search history.

(56) References Cited

U.S. PATENT DOCUMENTS

2019/0201698 A1     7/2019     Herrmann et al.
2019/0290918 A1     9/2019     Ghosh \* cited by examiner

IMPLANTABLE MEDICAL DEVICE FOR STIMULATING THE HIS BUNDLE OF A HUMAN OR ANIMAL HEART EMPLOYING AN IMPROVED DISTINCTION BETWEEN ATRIAL AND VENTRICULAR SIGNALS DETECTED AT THE HIS BUNDLE

CROSS-REFERENCE TO RELATED APPLICATIONS

This application is the United States National Phase under 35 U.S.C. § 371 of PCT International Patent Application No. PCT/EP2020/079741, filed on Oct. 22, 2020, which claims the benefit of European Patent Application No. 19205046.6, filed on Oct. 24, 2019, the disclosures of which are hereby incorporated by reference herein in their entireties.

TECHNICAL FIELD

The present invention relates to an implantable medical device for stimulating a human or animal heart according to the preamble of claim 1, to a method for safely identifying a His bundle activity signal or a ventricular activity signal with such an implantable medical device according to the preamble of claim 8, and to a computer program product according to the preamble of claim 9.

BACKGROUND

Implantable medical devices for stimulating a human or animal heart, such as pacemakers, have been known for a long time. They can perform different functions. Different stimulation programs can be carried out by an appropriate pacemaker to restore the treated heart to a normal state. Pacemakers are also known to stimulate the His bundle.

The His bundle is a bundle of specific heart muscle cells that is part of the cardiac conduction system. The His bundle is located distally of the atrioventricular node towards the apex of the heart.

There exist devices adapted for His bundle pacing, wherein a detecting (sensing) and stimulation electrode is not implanted into the ventricle of the human or animal heart to be treated, but rather at or near to the His bundle of the heart. Such use of a His bundle electrode enables a particularly physiologic stimulation of the human or animal heart.

However, depending on the concrete site of implantation of the His bundle electrode, it may be difficult to distinguish a signal being indicative for a ventricular activity from a signal being indicative for an atrial activity of the heart to be stimulated if both signals are detected with the His bundle electrode. If an atrial activity signal is erroneously considered to be a ventricular activity signal, a normal activity of the heart would be assumed, even though there is in fact no ventricular activity. In such a case, a stimulation of the His bundle (His bundle pacing) would be inhibited, even though it would be required. Obviously, severe medical conditions may result from such an incorrect interpretation of an atrial activity signal.

The present disclosure is directed toward overcoming one or more of the above-mentioned problems, though not necessarily limited to embodiments that do.

SUMMARY

It is an object of the present invention to provide an implantable medical device for sensing electric signals at the His bundle of a human or animal heart that enables a reliable distinction between ventricular activity signals and atrial activity signals.

At least this object is achieved with an implantable medical device for stimulating a human or animal heart having the features of claim 1. Such a device comprises a processor, a memory unit, a stimulation unit, a first detection unit and a second detection unit. The stimulation unit is configured to stimulate the His bundle of a human or animal heart. The first detection unit is configured to detect an electric signal at an atrium of the same heart, in particular of the right atrium of the same heart. The second detection unit is configured to detect an electric signal at the His bundle of the heart.

The memory unit comprises a computer-readable program that causes the processor to perform the steps explained in the following when executed on the processor.

First, an atrial electric signal is detected with the first detection unit at an atrium of the heart, in particular at the right atrium of the heart.

Furthermore, an electric signal at the His bundle is detected with the second detection unit. However, this detection is only started upon termination of a first time period. This first time period starts upon sensing the atrial electric signal with the first detection unit and/or starting upon applying a stimulation pulse. In this context, the first time period lies in a range of from 10 ms to 100 ms, in particular of from 15 ms to 90 ms, in particular of from 20 ms to 80 ms, in particular of from 25 ms to 70 ms, in particular of from 30 ms to 60 ms, in particular of from 40 ms to 50 ms.

The electric signal that has been detected with the second detection unit after termination of the first time period is then classified as a His bundle activity signal or as a ventricular activity signal. Thus, the implantable medical device excludes that the electric signal detected with the second detection unit after expiration of the first time period is an atrial activity signal.

The first time period can also be denoted as a blanking period or blanking window. It serves for blanking a detection or sensing of electric signals at the His bundle during the first time period. The first period is chosen such that electric signals deriving from an atrial activity of the heart fall into the first time period and will thus not be detected by the second detection unit (the second detection unit typically comprising a His bundle electrode). However, electric signals occurring after the end of the first time period originate from a His bundle activity or from a ventricular activity detected at the His bundle. Thus, these electric signals can be safely classified as a His bundle activity signal or a ventricular activity signal.

Thus, the implantable medical device employs suppression of detection of atrial signals with the second detection unit so that it eliminates the risk of mixing up atrial signals with ventricular signals detected with the second detection unit. This, in turn, results in an enhanced reliability of the operation of the implantable medical device and a reduction of the risk of undesired severe side effects due to incorrect inhibition of His bundle pacing.

In an embodiment, the blanking effected by the first time period is carried out as far-field blanking.

In an embodiment, the implantable medical device is an implantable pulse generator (IPG), an implantable cardioverter-defibrillator (ICD), or a device for cardiac resynchronization therapy (CRT).

In an embodiment, the computer-readable program causes the processor to set a first sensing threshold prior to the step of sensing an electric signal at the His bundle with the second detection unit. In this context, the first sensing threshold is lower than a His bundle activity signal when detected with the second detection unit, but higher than noise that is typically expected to be detected with the second detection unit. By setting such a first sensing threshold, no noise will be detected any longer, whereas a safe detection of a His bundle activity signal and more intense signals is still possible. Thus, when applying the first sensing threshold, it is possible to detect both a His bundle activity signal and a ventricular activity signal with the second detection unit. In an embodiment, the first sensing threshold is determined by a test measurement aimed at determining a noise level prior to setting the first sensing threshold. Such an approach is often particularly appropriate since the concrete noise level strongly depends on the implantation circumstances and physiologic characteristics of the heart to be stimulated.

In an embodiment, the computer-readable program causes the processor to set a second sensing threshold prior to the step of sensing an electric signal at the His bundle with the second detection unit. In this context, the second sensing threshold is higher than a His bundle activity signal when detected with the second detection unit. At the same time, the second sensing threshold is lower than a ventricular activity signal when detected with the second detection unit. Thus, the second sensing threshold can be set to distinguish a ventricular activity signal from a His bundle activity signal. If the detected electric signal exceeds the second sensing threshold, the electric signal sensed with the second detection unit will consequently be classified as ventricular activity signal. In an embodiment, an appropriate value for the second sensing threshold is determined prior to setting the second sensing threshold. This can be done—as in case of the first sensing threshold—by a test measurement (cf. explanations in the preceding paragraph).

In an embodiment, both the first sensing threshold and the second sensing threshold are set, wherein the first sensing threshold serves for no signals being sensed falling below the first sensing threshold, whereas the second sensing threshold serves for distinguishing between a His bundle activity signal and a ventricular activity signal and still allows, in this embodiment, to detect signals generally falling below the second sensing threshold.

In an embodiment, the computer-readable program causes the processor to set a marker for the electric signal sensed with the second detection unit. This marker comprises two kinds of information. The first information is information on the type of the electric signal. It reflects the classifying of the electric signal. Thus, this information can be "His bundle activity" or "ventricular activity". The second kind of information is a time information. It reflects a delayed sensing time. In this context, the delayed sensing time is defined to be an original sensing time plus a delay time. The delay time is shorter than the first time period and lies in a range of from 0 to 50 ms, in particular of from 5 ms to 45 ms, in particular of from 10 ms to 40 ms, in particular of from 20 ms to 30 ms. The electric signal is only classified as a His bundle activity signal or as a ventricular activity signal if the delayed sensing time of the marker does not fall into the first time period.

Due to the delayed sensing time, the marker occurs in a timeline of markers later than the original signal for which the marker was set. Thus, the delayed sensing time serves for a shift of the marker to a later time point. In doing so, one can make sure that the marker that would be set for an atrial activity reliably falls into the first time period and is thus not detected.

Without such delay time, the following situation might be generally possible under special circumstances: An atrial electric signal is detected with the first detection unit. Upon detection of this atrial electric signal and/or upon applying a stimulation pulse, the first time period starts. However, there is a very small delay in the start of the first time period due to the time necessary for signal transduction. The atrial activity gives also rise to a signal that can be detected with the second detection unit. If this atrial activity signal is detected with the second detection unit at the same time as the atrial activity signal with the first detection unit, but slightly prior to the start of the first time period (blanking period), the second detection unit would, in fact, detect an electric signal and would wrongly assign it to be a His bundle activity signal or a ventricular activity signal. If, however, a delay time is applied to a marker set for the signal, this marker is shifted into the first time period and thus serves for suppressing a detection of an atrial activity signal with the second detection unit.

In an embodiment, a similar delay approach is taken, but not with respect to a temporal adjustment of a marker set for a specific electric signal, but rather for the electric signal itself. In this embodiment, the computer-readable program causes the processor to delay all electric signals sensed by the second detection unit by a delay time. This delay time is shorter than the first time period lies in a range of from 0 to 50 ms, in particular of from 5 ms to 45 ms, in particular of from 10 ms to 40 ms, in particular of from 20 ms to 30 ms. This delay time results in a different timescale for signals detected with the second detection unit than for signals detected with the first detection unit. While such a temporal shift of the specific channel (i.e., the His channel in case of the second detection unit) might make an evaluation of an intracardiac electrogram (IEGM) more difficult for a physician, such temporal shift of all electric signals detectable with the second detection unit has basically the same effect as applying a delay time to markers set for specific electric signals.

In an embodiment, the computer-readable program causes the processor to set a marker for the classified electric signal sensed with the second detection unit, wherein the marker comprises an information on a type of the electric signal and a time information. In this embodiment, the information on the type of the electric signal reflects once again the classifying of the electric signal. The time information reflects a sensing time already comprising the delay time. The electric signal is only classified as a His bundle activity signal or as a ventricular activity signal if the sensing time (already comprising the delay time) does not fall into the first time period. Thus, also this embodiment enables the use of a marker for a specific electric signal, but does not serve for a delay of the marker with respect to the detected signal, but rather to delay of the detected signal itself. Consequently, the marker and the electric signal for which the marker was set correspond in time, but are both shifted with respect to a real occurrence of the electric signal in the heart. Also in this embodiment, an atrial electric signal detected with the second detection unit can be shifted into the first time period (blanking period) so that the risk of accidentally detecting an atrial activity signal with the second detection unit can be further reduced.

In an embodiment, the implantable medical device comprises a stimulation unit that serves for stimulating an atrium of the heart, in particular a right atrium of the heart. In such a case, it is not only possible to detect an atrial electric signal with the first detection unit, but also to perform an atrial pacing with the further stimulation unit. Such an atrial pacing will immediately result in an atrial electric signal that can be detected with the first detection unit. Thus, the first time period starting upon detection of an electric signal with the first detection unit can also directly be started upon performing an atrial pacing since there will be no technical difference if the start point of the first time period is triggered with an applied atrial pacing or with a detection of atrial electric signal with the first detection unit in response to such pacing.

In an aspect, the present invention relates to a method for safely identifying a His bundle activity signal or a ventricular activity signal by a detection unit of an implantable medical device according to the preceding explanations. This method comprises the steps explained in the following.

First, an atrial electric signal is detected with a first detection unit configured to detect an electrical signal at an atrium of a human or animal heart, in particular at the right atrium of the heart.

Furthermore, an electric signal at the His bundle is detected with a second detection unit. However, this detection is only started upon termination of a first time period. This first time period starts upon sensing the atrial electric signal with the first detection unit. In this context, the first time period lies in a range of from 10 ms to 100 ms.

The electric signal that has been detected with the second detection unit after termination of the first time period is then classified as a His bundle activity signal or as a ventricular activity signal. Thus, the method excludes that the electric signal detected with the second detection unit after expiration of the first time period is an atrial activity signal.

In an aspect, the present invention relates to a computer program product comprising computer-readable code that causes the processor to perform the steps explained in the following when executed on the processor.

First, an atrial electric signal is detected with a first detection unit configured to detect an electrical signal at an atrium of a human or animal heart, in particular at the right atrium of the heart.

Furthermore, an electric signal at the His bundle is detected with a second detection unit. However, this detection is only started upon termination of a first time period. This first time period starts upon sensing the atrial electric signal with the first detection unit. In this context, the first time period lies in a range of from 10 ms to 100 ms.

The electric signal that has been detected with the second detection unit after termination of the first time period is then classified as a His bundle activity signal or as a ventricular activity signal.

In an aspect, the present invention relates to a method of treating a human or animal patient in need of such treatment with an implantable medical device for stimulating a human or animal heart. Such a device comprises a processor, a memory unit, a stimulation unit, a first detection unit and a second detection unit. The stimulation unit is configured to stimulate the His bundle of a human or animal heart. The first detection unit is configured to detect an electric signal at an atrium of the same heart, in particular of the right atrium of the same heart. The second detection unit is configured to detect an electric signal at the His bundle of the heart. This method comprises the steps explained in the following.

First, an atrial electric signal is detected with the first detection unit at an atrium of the heart, in particular at the right atrium of the heart.

Furthermore, an electric signal at the His bundle is detected with the second detection unit. However, this detection is only started upon termination of a first time period. This first time period starts upon sensing the atrial electric signal with the first detection unit and/or starting upon applying a stimulation pulse. In this context, the first time period lies in a range of from 10 ms to 100 ms.

The electric signal that has been detected with the second detection unit after termination of the first time period is then classified as a His bundle activity signal or as a ventricular activity signal. Thus, the implantable medical device excludes that the electric signal detected with the second detection unit after expiration of the first time period is an atrial activity signal.

Finally, the His bundle is stimulated with the stimulation unit if no ventricular activity signal has been sensed during a second time period. In this context, the second time period starts upon sensing the atrial electric signal with the first detection unit. Furthermore, the second time period lies in a range of from 15 ms to 300 ms, in particular of from 30 ms to 150 ms, in particular of from 40 ms to 120 ms. An absence of any ventricular activity over such a period of time is a medical indication for pacing the heart in order to maintain cardiac activity and, optimally, restoring the natural cardiac activity.

All embodiments of the implantable medical device can be combined in any desired way and can be transferred either individually or in any arbitrary combination to the described methods and the described computer program product. Likewise, all embodiments of the described methods can be combined in any desired way and can be transferred either individually or in any arbitrary combination to the respective other method, to the implantable medical device and to the computer program product. Finally, all embodiments described with respect to the computer program product can be combined in any desired way and can be transferred either individually or in any arbitrary combination to the described implantable medical device or to the described methods.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

Further details of aspects of the present invention will be described in the following making reference to exemplary embodiments and accompanying Figures. In the Figures.

DETAILED DESCRIPTION

Figure 1A:
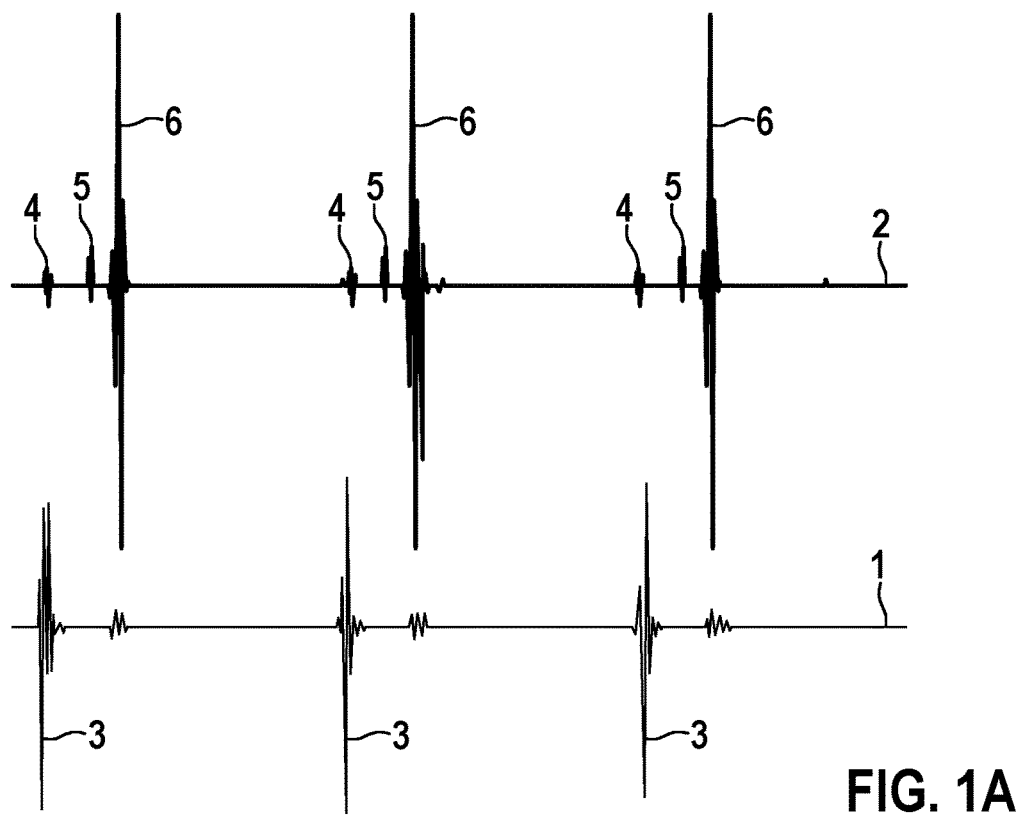
FIG. 1A shows a first intracardiac electrogram comprising signals of two channels.

FIG. 1A shows a first intracardiac electrogram obtained with a pacemaker as implantable medical device. This first intracardiac electrogram comprises signals of a first channel 1 and signals of the second channel 2. The first channel 1 reflects signals obtained with an atrial detection unit serving as first detection unit configured to detect an electric signal at an atrium of the human or animal heart. The second channel 2 comprises signals obtained with a His bundle detection unit serving as second detection unit configured to detect an electrical signal at the His bundle of the same heart.

In the first channel 1, a couple of atrial activity signals 3 can be observed. In the second channel 2, very small atrial deflections 4, more prominent His bundle deflections 5 and strong ventricular deflections 6 can be observed.

This intracardiac electrogram is representative for a distal placement of a His bundle electrode used for obtaining the His bundle signal, i.e., the signal of the second channel 2. In such an optimal implantation position, a clear distinction can be made between the atrial deflections 4 on the one hand and the ventricular deflections 6 on the other hand. It is rather unlikely that an atrial deflection 4 will be erroneously considered to be ventricular deflections 6 so that no inadvertent inhibition of His bundle pacing is likely to occur.

Figure 1B:
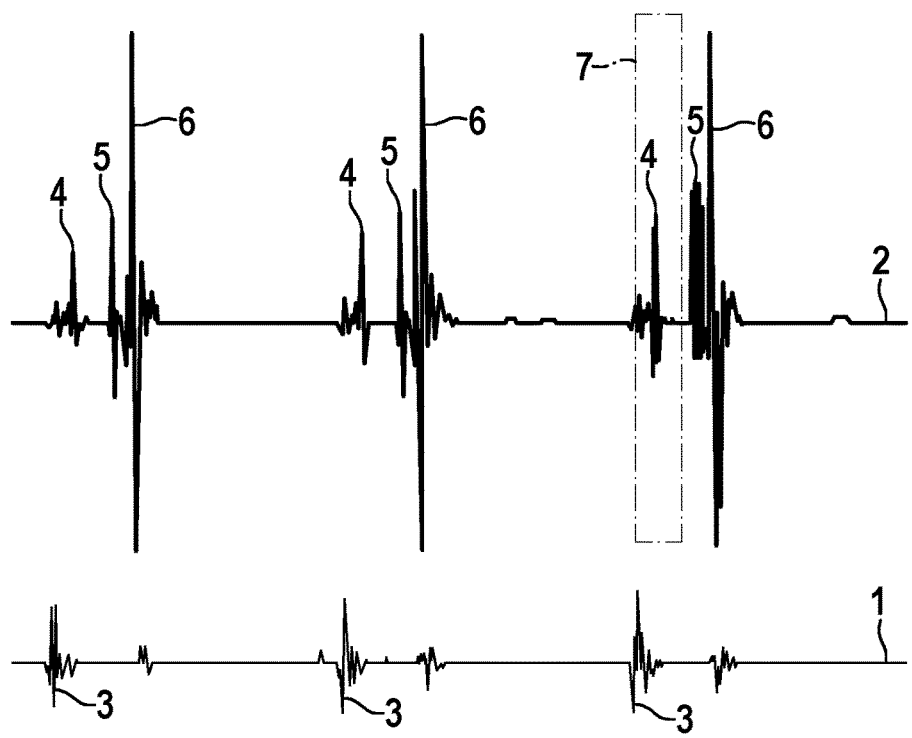
FIG. 1B shows a second intracardiac electrogram comprising signals of two channels.

However, such an optimal implantation position is not the standard. FIG. 1B shows an intracardiac electrogram obtained once again with an atrial detection unit (giving rise to the signals in the first channel 1) and a His bundle detection unit (giving rise to the signals in the second channel 2). In this and all following Figures similar elements will be denoted with the same numeral references.

In contrast to the setting of FIG. 1A, the His bundle electrode is implanted on a proximal implantation site in the embodiment of FIG. 1B. Whereas atrial activity signals 3 can well be observed in the first channel 1 delivered by the atrial detection unit, a distinction between atrial deflections 4, His bundle deflections 5 and ventricular deflections 6 in the His bundle signal of the second channel 2 becomes more difficult. This is due to the fact that the atrial deflections 4 are much stronger due to the proximal implantation site of the His bundle electrode.

In such a setting, a blanking window 7 is applied serving as first time period. This blanking window 7 starts upon the detection of an atrial activity signal 3 in the first channel 1 and has a duration of approximately 60 ms. Thus, it will cover an atrial deflection 4 in the His bundle signal of the second channel 2, but will not cover the His bundle deflections 5 nor the ventricular deflections 6 detected by the His bundle electrode and displayed in the second channel 2.

The blanking window 7 has the effect that all signals falling within this blanking window will not be detected by the His bundle detection unit. Rather, the according detection will be suppressed by the blanking window 7. Consequently, no atrial deflection 4 in the His bundle signal of the second channel 2 will be detected any longer if the blanking window 7 is applied to this signal. In contrast, the His bundle deflection 5 (indicative for a His bundle activity) and the ventricular deflection 6 (indicative for a ventricular activity) will still be detected. Consequently, an inadvertent misinterpretation of an atrial deflection 4 to be a ventricular activity signal in the second channel 2 is no longer possible.

Figure 1C:
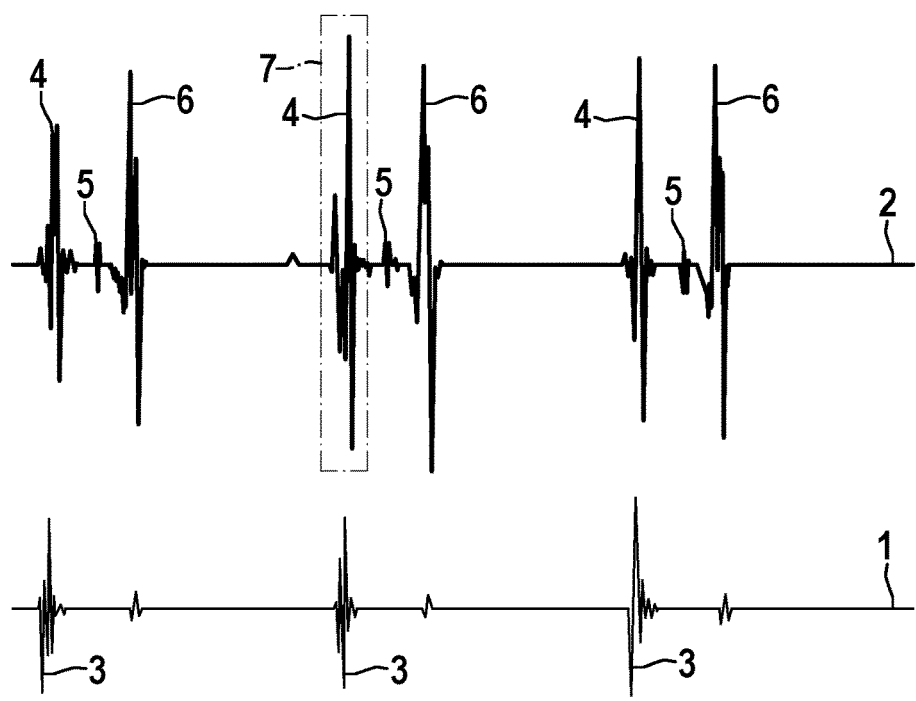
FIG. 1C shows a third intracardiac electrogram comprising signals of two channels.

The application of such a blanking window 7 is also helpful in case of a very proximal implantation of the His bundle electrode. In such a case, an intracardiac electrogram as shown in FIG. 1C is obtained. Here, an atrial over-sensing takes place leading to an atrial deflection 5 being as strong as or even stronger than a ventricular deflection 6 in the His bundle electrode signal detected in the second channel 2 of the intracardiac electrogram. Also in this case, a blanking window 7 serves for suppressing detection of the atrial deflection 4 so that the resulting deflections can be identified as His bundle deflections 5 and ventricular deflections 6.

Figure 2A:
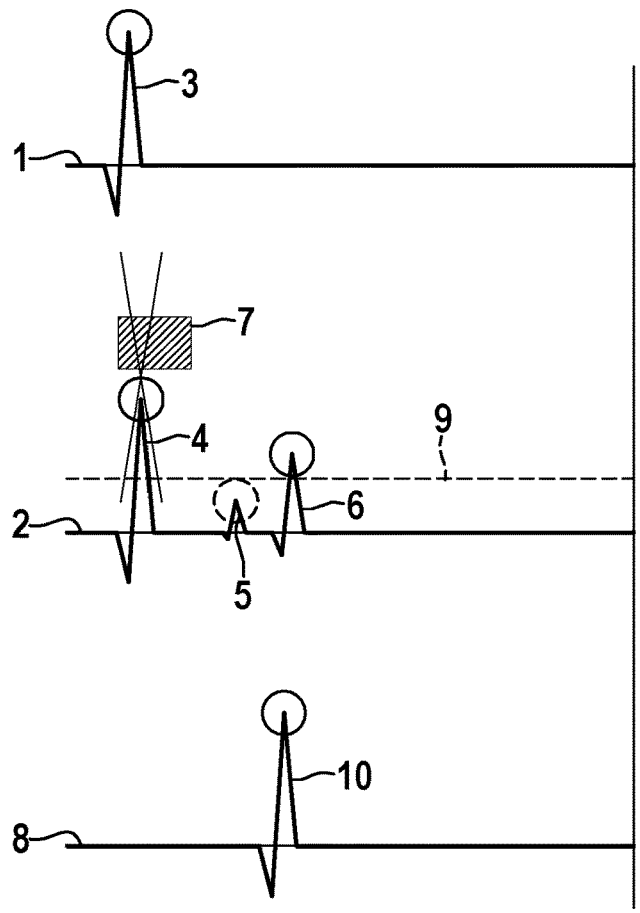
FIG. 2A shows a first simulated intracardiac electrogram comprising signals of three channels.

FIG. 2A schematically depicts a first simulated intracardiac electrogram comprising signals of three channels, namely a right atrial channel 1, a His bundle channel 2 and an apical channel 8. The right atrial channel 1 indicates electrical signals sensed with a right atrial electrode connected to a right atrial port of a pacemaker serving as implantable medical device. Here, an atrial electric signal 3 can be detected (atrial sense in atrial signal).

The His bundle channel 2 reflects signals detected by a His bundle electrode connected to a right ventricular port of the pacemaker. Here, also an atrial signal can be observed, namely an atrial deflection 4. It occurs basically at the same time as the atrial signal 3 in the right atrial channel 1. However, due to the application of a blanking window 7, the detection of the atrial deflection 4 is suppressed. Expressed in other words, the blanking window 7 serves for blanking the detection of an atrial activity signal in the His bundle channel 2.

Generally, a His bundle deflection 5 could be observed in the His bundle channel 2. However, prior to detecting the signals, a sensing threshold 9 was set which is higher than the His bundle deflection 5. Therefore, this His bundle deflection 5 will not be detected.

However, a ventricular deflection 6 can be observed in the His bundle channel 2 since it lies outside the blanking period 7 and has an intensity exceeding the sensing threshold 9. Consequently, the His bundle channel 2 will only comprise a single detected deflection, namely the ventricular deflection 6.

The apical channel 8 is recorded with a right ventricular electrode that is connected to the left ventricular port of the pacemaker (since the right ventricular port is already occupied by the His bundle electrode). This right ventricular electrode serves as backup electrode for the His bundle electrode. In this apical channel 8, a strong right ventricular deflection 10 can be observed indicating a ventricular contraction.

Figure 2B:
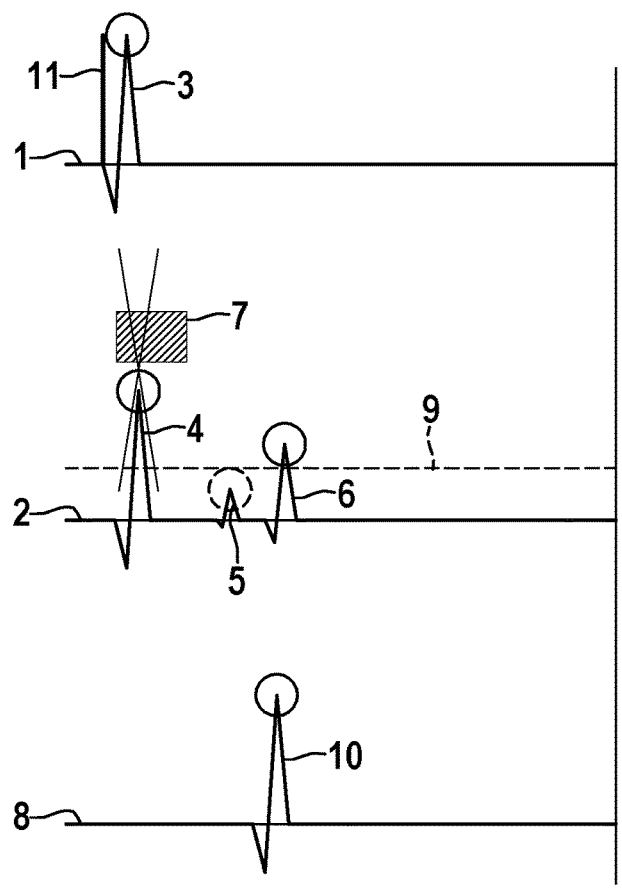
FIG. 2B shows a second simulated intracardiac electrogram comprising signals of three channels.

FIG. 2B shows a second simulated intracardiac electrogram being very similar to the first simulated intracardiac electrogram of FIG. 2A. Therefore, reference is made to the explanations given with respect to FIG. 2A for explaining FIG. 2B. The only difference between FIG. 2A and FIG. 2B is that in case of FIG. 2B, no intrinsic atrial deflection 3 is observed in the right atrial channel 1, but rather an atrial deflection 3 caused in response to an atrial pace 11. However, the consequences for blanking an atrial deflection 4 in His bundle channel 2, for suppressing a detection of a His bundle deflection 5 due to a sensing threshold 9 and for being able to detect a ventricular deflection 6 in the His bundle channel 2 remain the same. The blanking window 7 serves for efficient suppression of a detection of the atrial deflection 4 in the His bundle channel 2.

Also in this embodiment, the apical channel 8 still comprises a strong ventricular deflection 10 being indicative for a ventricular contraction.

Figure 3:
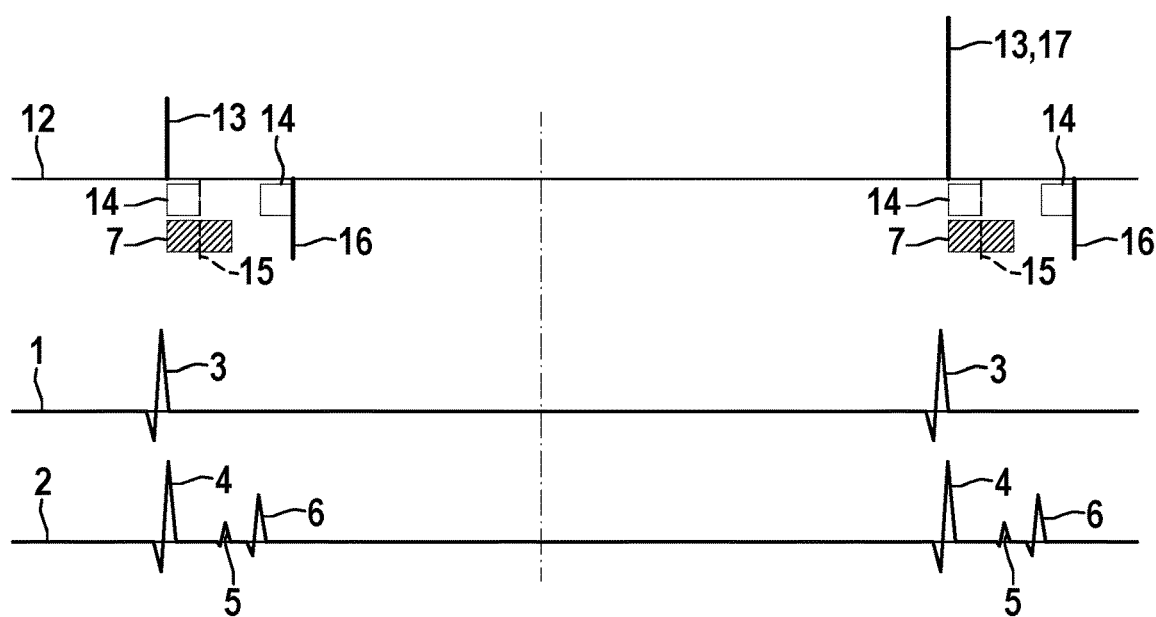
FIG. 3 shows a third simulated intracardiac electrogram comprising signals of two channels and marker signals.

FIG. 3 shows a third stimulated intracardiac electrogram and makes reference to the situations depicted in FIGS. 2A and 2B. Turning first to the left-hand side of FIG. 3 (with particular reference to the explanations given with respect to FIG. 2A), this stimulated intracardiac electrogram comprises a right atrial channel 1 and a His bundle channel 2. In addition, a marker channel 12 is displayed.

Upon detection of an atrial deflection 3 in the atrial channel 1, an atrial marker 13 is set in the marker channel 12. The atrial marker 13 indicates on the one hand that the detected signal is in atrial signal and on the other hand the time point of detection of this atrial signal.

An atrial deflection 4 in the His bundle channel 2 is subjected to a delay time 14 prior to setting a marker. Consequently, an atrial marker 15 would be set at a time in the marker channel 12 that corresponds to the real occurrence of the underlying atrial deflection 4 plus the delay time 14. However, such an atrial marker 15 would directly fall into the blanking window 7 and will thus not be set; the blanking window 7 suppresses setting of the atrial marker 15. A His bundle deflection 5 in the His bundle channel 2 will not be detected due to the applied sensing threshold (cf. FIGS. 2A and 2B). However, a ventricular deflection 6 exceeds this sensing threshold and will be detected. When setting a marker for this ventricular deflection 6, the same delay time 14 as in case of the atrial deflection 4 is added to the real time of detection. Consequently, a ventricular marker 16 is set in the marker channel 12 at a time corresponding to the real occurrence of the ventricular deflection 6 plus the delay time 14.

In case of the ventricular deflection 6, the delay time 14 has no influence on suppressing or recording the corresponding ventricular marker 16. This is due to the fact that the ventricular marker 16 is set at a time point which does not fall into the blanking period 7, neither with nor without application of the delay time 14. Consequently, the ventricular marker 16 will be set. This results in two markers being present in the marker channel 12, namely the atrial marker 13 indicative for an atrial activity 3 sensed in the atrium as well as a ventricular activity 16 sensed by the His bundle electrode. This, in turn, indicates normal cardiac activity so that no stimulation of the heart is necessary.

Turning now to the right-hand side of FIG. 3, a situation will be explained in which such a stimulation is necessary. Consequently, an atrial pace 11 (cf. FIG. 2B) is applied. Then, an atrial pace marker 17 is set in the marker channel 12. This atrial pace marker 17 is set at the same time as an atrial marker 13 being indicative for an atrial activity identified by an atrial deflection 3 in the atrial channel 1. Also in this case, the delay time 14 is applied to an atrial deflection 4 as well as to a ventricular deflection 6 in the His bundle channel 2. An atrial marker 15 for the atrial deflection 4 would fall again into the blanking window 7 and will thus not be set to the marker channel 12. In contrast, a ventricular marker 16 will be set so that the resulting marker channel 12 comprises the atrial marker 13 serving at the same time as atrial pace marker 17 as well as the ventricular marker 16. Thus, there is positive knowledge that the atrial pacing resulted in a ventricular activity, i.e., that the atrial pacing was successful.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

The invention claimed is:

1. Implantable medical device, comprising:
   a processor, a memory unit, a stimulation unit configured to generate a stimulation pulse to stimulate the His bundle of the human or animal heart, a first detection unit configured to detect an electrical signal at an atrium of the same heart, and a second detection unit configured to detect an electrical signal at the His bundle of the same heart,
   wherein the memory unit comprises a computer-readable program that causes the processor to perform the following steps when executed on the processor:
   a) sense an atrial electric signal with the first detection unit, and transmit the atrial electric signal to the processor;
   b) sense an electric signal at the His bundle with the second detection unit upon termination of a first time period starting upon sensing the atrial electric signal with the first detection unit and/or starting upon applying a stimulation pulse, wherein the first time period lies in a range of from 10 ms to 100 ms, and transmit the electric signal to the processor;
   c) classify the electric signal sensed with the second detection unit as His bundle activity signal or as ventricular activity signal;
   d) stimulate the His bundle with the stimulation unit if no ventricular activity signal has been sensed during a second time period starting upon sensing the atrial electric signal with the first detection unit, wherein the second time period lies in a range of from 15 ms to 300 ms.

2. The implantable medical device according to claim 1, wherein the computer-readable program causes the processor to set a first sensing threshold, wherein the first sensing threshold is lower than the His bundle activity signal when detected with the second detection unit, but higher than typically expected noise.

3. The implantable medical device according to claim 1, wherein the computer-readable program causes the processor to set a second sensing threshold, wherein the second sensing threshold is higher than the His bundle activity signal when detected with the second detection unit, but lower than a ventricular activity signal when detected with the second detection unit, and to classify the electric signal sensed with the second detection unit as ventricular activity signal if the electric signal exceeds the second sensing threshold.

4. The implantable medical device according to claim 1, wherein the computer-readable program causes the processor to set a marker for the electric signal sensed with the second detection unit, the marker comprising an information on a type of the electric signal reflecting the classification of the electric signal and a time information reflecting a delayed sensing time, wherein the delayed sensing time is calculated as original sensing time plus a delay time, wherein the delay time is shorter than the first time period and lies in a range of from 0 to 50 ms, wherein the electric signal is only classified as the His bundle activity signal or as the atrial activity signal if the delayed sensing time does not fall into the first time period.

5. The implantable medical device according to claim 1, wherein the computer-readable program causes the processor to delay all electric signals sensed by the second detection unit by a delay time, wherein the delay time is shorter than the first time period and lies in a range of from 0 to 50 ms.

6. The implantable medical device according to claim 5, wherein the computer-readable program causes the processor to set a marker for the electric signal sensed with the second detection unit, the marker comprising an information on a type of the electric signal reflecting the classifying of the electric signal and a time information reflecting a sensing time already comprising the delay time, wherein the electric signal is only classified as the His bundle activity signal or as the atrial activity signal if the sensing time does not fall into the first time period.

7. The implantable medical device according to claim 1, wherein the implantable medical device comprises a further stimulation unit configured to stimulate an atrium of the same heart.

8. A computer program product comprising computer-readable code that causes a processor to perform the following steps when executed on the processor:
- a) receive an atrial electric signal from a first detection unit;
- b) receive an electric signal related to His bundle activity from a second detection unit upon termination of a first time period starting upon sensing the atrial electric signal with the first detection unit and/or starting upon applying a stimulation pulse, wherein the first time period lies in a range of from 10 ms to 100 ms;
- c) classify the electric signal sensed with the second detection unit as His bundle activity signal or as ventricular activity signal;
- d) stimulate the His bundle with a stimulation unit if no ventricular activity signal has been sensed during a second time period starting upon sensing the atrial electric signal with the first detection unit, wherein the second time period lies in a range of from 15 ms to 300 ms.

9. A method of treatment of a human or animal patient in need of such treatment with an implantable medical device for stimulating the human or animal heart, the implantable medical device comprising a processor, a memory unit, a stimulation unit configured to stimulate the His bundle of the human or animal heart, a first detection unit configured to detect an electrical signal at an atrium of the same heart, and a second detection unit configured to detect an electrical signal at the His bundle of the same heart, the method comprising the following steps:
- a) sensing an atrial electric signal with the first detection unit;
- b) sensing an electric signal at the His bundle with the second detection unit upon termination of a first time period starting upon sensing the atrial electric signal with the first detection unit and/or starting upon applying a stimulation pulse, wherein the first time period lies in a range of from 10 ms to 100 ms;
- c) classifying the electric signal sensed with the second detection unit as His bundle activity signal or as ventricular activity signal; and
- d) stimulating the His bundle with the stimulation unit if no ventricular activity signal has been sensed during a second time period starting upon sensing the atrial electric signal with the first detection unit, wherein the second time period lies in a range of from 15 ms to 300 ms.

* * * * *